(12) United States Patent
Park et al.

(10) Patent No.: US 9,328,069 B2
(45) Date of Patent: May 3, 2016

(54) CATALYTIC MANUFACTURING METHOD FOR IMINE HAVING NO SUBSTITUENT GROUP ON THE NITROGEN, AND USE FOR THE IMINE PRODUCED

(71) Applicant: POSTECH ACADEMY-INDUSTRY FOUNDATION, Gyeongsangbuk-do (KR)

(72) Inventors: Jai Wook Park, Gyeongsanbuk-do (KR); Young Ho Rhee, Gyeongsanbuk-do (KR); Jin Hee Lee, Seoul (KR); Jung Hoon Han, Gyeonggi-do (KR); Sreya Gupta, Bazar (KR); Wook Jeong, Ulsan (KR)

(73) Assignee: Postech Academy-Industry Foundation (KR)

( * ) Notice: Subject to any disclaimer, the term of this patent is extended or adjusted under 35 U.S.C. 154(b) by 0 days.

(21) Appl. No.: 14/760,828

(22) PCT Filed: Mar. 28, 2013

(86) PCT No.: PCT/KR2013/002599
§ 371 (c)(1),
(2) Date: Jul. 14, 2015

(87) PCT Pub. No.: WO2014/112688
PCT Pub. Date: Jul. 24, 2014

(65) Prior Publication Data
US 2015/0344428 A1    Dec. 3, 2015

(30) Foreign Application Priority Data

Jan. 16, 2013  (KR) .................. 10-2013-0005130

(51) Int. Cl.
*C07F 7/18*     (2006.01)
*C07D 213/74*   (2006.01)
(Continued)

(52) U.S. Cl.
CPC .............. *C07D 213/74* (2013.01); *B01J 31/12* (2013.01); *B01J 31/16* (2013.01); *B01J 31/2295* (2013.01);
(Continued)

(58) Field of Classification Search
CPC ..... C07F 17/02; C07F 7/1892; C07D 213/74; B01J 31/2295; C07C 221/00; C07C 209/52; C07C 253/30; C07C 249/02
USPC ............. 546/329; 556/413; 558/422; 560/37, 560/172; 564/248, 509
See application file for complete search history.

(56) References Cited

FOREIGN PATENT DOCUMENTS

JP    2002265430    9/2002

OTHER PUBLICATIONS

Albertin et al., "Preparation of imine complexes of ruthenium and osmium stabilized by [MCl($\eta^6$-p-cymene)(PR$_3$)]+ fragments," *Journal of Ogranometallic Chemistry*, 2010, 695:574-579.
(Continued)

*Primary Examiner* — Porfirio Nazario Gonzalez
(74) *Attorney, Agent, or Firm* — Riverside Law LLP (57) ABSTRACT

The present invention relates to a method for manufacturing an imine having no substituent group on the nitrogen by using, as a catalyst, a metal complex on an organic azide compound, and more specifically relates to a method in which a metal-complex catalyst is used to produce, from an organic azide having an alpha-hydrogen, an imine having no substituent group on the nitrogen via a continuous nitrogen removal and 1,2-hydrogen transfer reaction. The imine having no substituent group on the nitrogen manufactured by means of the method of the present invention can synthesize diverse coupling products comprising amine compounds by means of reactions with diverse nucleophiles.

7 Claims, 4 Drawing Sheets

Reaction Formula 1

In Reaction Formula 1, $R_1$ and $R_2$ are each independently hydrogen, substituted or unsubstituted phenyl, or $C_1$~$C_5$ alkyl.

(51) Int. Cl.
| | |
|---|---|
| *B01J 31/22* | (2006.01) |
| *C07C 209/52* | (2006.01) |
| *C07C 249/02* | (2006.01) |
| *C07C 253/30* | (2006.01) |
| *C07C 221/00* | (2006.01) |
| *B01J 31/12* | (2006.01) |
| *B01J 31/16* | (2006.01) |
| *C07F 15/00* | (2006.01) |
| *C07F 17/02* | (2006.01) |

(52) U.S. Cl.
CPC ............ *C07C 209/52* (2013.01); *C07C 221/00* (2013.01); *C07C 249/02* (2013.01); *C07C 253/30* (2013.01); *C07F 7/1892* (2013.01); *C07F 15/0046* (2013.01); *C07F 17/02* (2013.01); *B01J 2531/821* (2013.01)

(56) References Cited

OTHER PUBLICATIONS

Boyd et al., "Base Catalysed Decomposition of Oxaziridines to Yield N-Unsubstituted Aldimines," *Tetrahedron Letters* No. 34, 1979, pp. 3201-3204.

Chen et al., "The Critical Importance of Water in the Asymmetric Allylboration of N-Trimethylsilylbenzaldimines with B-Allyldiisopinocampheylborane," *Angew. Chem. Int. Ed.*, 1999, 38(6):825-826.

Chiba et al., "Copper-Catalyzed Synthesis of Azaspirocyclohexadienones from α-Azido-N-arylamides under an Oxygen Atmosphere," *J. Am. Chem. Soc.*, 2010, 132:7266-7267.

Dhudshia, et al. "Diastereoselective allylation and crotylation of N-unsubstituted imines derived from ketones," *Chem. Commun.*, 2005, pp. 5551-5553.

Han et al., "N-unsubstituted Imines: Ru-catalyzed Synthesis from Alkyl Azides, Characterization, and the Utility," The Korean Chemical Society 110th Conference and abstract of Symposium poster presentation, Oct. 17, 2012.

Lee et al., "Characterization and Utility of N-Unsubstituted Imines Synthesized from Alkyl Azides by Ruthenium Catalysis," *Angew. Chem. Int. Ed.*, 2012, 51:10851-10855.

Risse et al., "Beyond Click-Chemistry: Transformation of Azides with Cyclopentadienyl Ruthenium Complexes," *Organometallics*, 2011, 30:3412-3418.

Sugiura et al., "α-Aminoallylation of Aldehydes with Ammonia: Stereoselective Synthesis of Homoallylic Primary Amines," *J. Am. Chem. Soc.*, 2004, 126:7182-7183.

Fig. 1

Reaction Formula 1

In Reaction Formula 1, $R_1$ and $R_2$ are each independently hydrogen, substituted or unsubstituted phenyl, or $C_1$~$C_5$ alkyl.

Fig. 2

| Example | Azide | Amine | Product | Yield(%) |
|---|---|---|---|---|
| 2-1 | Ph$\sim$N$_3$ | $\sim\sim\sim$NH$_2$ | Ph$\sim$N$\sim\sim\sim$ | 95 |
| 2-2 | Ph$\sim$N$_3$ | Cy-NH$_2$ | Ph$\sim$N-Cy | 97 |
| 2-3 | Ph$\sim$N$_3$ | t-Bu-NH$_2$ | Ph$\sim$N-t-Bu | 48 |
| 2-4 | Ph$\sim$N$_3$ | allyl-NH$_2$ | Ph$\sim$N-allyl | 99 |
| 2-5 | Ph$\sim$N$_3$ | H$_2$N$\sim$CH(Et)$\sim$NH$_2$ | cyclic (Ph, Et, HN, NH) | 89 |
| 2-6 | Ph$\sim$N$_3$ | Ph$\sim$NH$_2$ | Ph$\sim$N$\sim$Ph | 95 |
| 2-7 | Ph$\sim$N$_3$ | 2-pyridyl-CH$_2$NH$_2$ | Ph$\sim$N$\sim$CH$_2$-2-pyridyl | 86 |
| 2-8 | 4-MeO-C$_6$H$_4$-CH$_2$-N$_3$ | $\sim\sim\sim$NH$_2$ | 4-MeO-C$_6$H$_4$-CH=N$\sim\sim\sim$ | 87 |
| 2-9 | 4-NC-C$_6$H$_4$-CH$_2$-N$_3$ | $\sim\sim\sim$NH$_2$ | 4-NC-C$_6$H$_4$-CH=N$\sim\sim\sim$ | 60 |
| 2-10 | 4-Br-C$_6$H$_4$-CH$_2$-N$_3$ | $\sim\sim\sim$NH$_2$ | 4-Br-C$_6$H$_4$-CH=N$\sim\sim\sim$ | 98 |
| 2-11 | Ph-CH$_2$CH$_2$-N$_3$ | $\sim\sim\sim$NH$_2$ | Ph-CH$_2$CH=N$\sim\sim\sim$ | 69 |
| 2-12 | $\sim\sim\sim\sim$N$_3$ | $\sim\sim\sim$NH$_2$ | $\sim\sim\sim\sim$N=$\sim\sim\sim$ | 96 |
| 2-13 | $\sim\sim\sim\sim$N$_3$ | Ph$\sim$NH$_2$ | $\sim\sim\sim$CH=N$\sim$Ph | 92 |
| 2-14 | Cy-N$_3$ | $\sim\sim\sim$NH$_2$ | Cy=N$\sim\sim\sim$ | 82 |

Fig. 3

| Example | Azide | Allyl boron compound | Product | Yield(%) |
|---|---|---|---|---|
| 3-1 | Ph-N₃ (benzyl azide) | allyl-B(pinacolate-tetramethyl) | Ph-CH(NH₂)-CH₂-CH=CH₂ | 83 |
| 3-2 | n-octyl-N₃ | | n-octyl-CH(NH₂)-CH₂-CH=CH₂ | 85 |
| 3-3 | MeO₂C-C₆H₄-CH₂-N₃ | | MeO₂C-C₆H₄-CH(NH₂)-CH₂-CH=CH₂ | 91 |
| 3-4 | EtO₂C-CH₂-N₃ | | EtO₂C-CH(NH₂)-CH₂-CH=CH₂ | 73 |
| 3-5 | cyclohexyl-N₃ | | 1-allyl-1-aminocyclohexane | 69 |
| 3-6 | Ph-CH₂-CH(OTBDMS)-CH₂-N₃ | | Ph-CH₂-CH(OTBDMS)-CH(NH₂)-CH₂-CH=CH₂ | 86 |
| 3-7 | 2-azido-1-OTBDMS-cyclohexane | | 1-allyl-1-amino-2-OTBDMS-cyclohexane | 80 |

Fig. 4

| Example | Azide | Allyl boron compound | Product | Yield(%) |
|---|---|---|---|---|
| 4-1 | PhCH₂N₃ | (E)-crotyl-Bpin | (1S,2S)-1-phenyl-2-methyl-3-buten-1-amine | 71 |
| 4-2 | PhCH₂N₃ | (Z)-crotyl-Bpin | (1S,2R)-1-phenyl-2-methyl-3-buten-1-amine | 80 |

CATALYTIC MANUFACTURING METHOD FOR IMINE HAVING NO SUBSTITUENT GROUP ON THE NITROGEN, AND USE FOR THE IMINE PRODUCED

CROSS-REFERENCE TO RELATED APPLICATIONS

This application is the U.S. national phase application filed under 35 U.S.C. §371 claiming benefit to International Patent Application No. PCT/KR2013/002599, filed on Mar. 28, 2013, which is entitled to priority under 35 U.S.C. §119(a)-(d) to Korean Patent Application No. 10-2013-0005130, filed Jan. 16, 2013, each of which application is hereby incorporated herein by reference in its entirety.

BACKGROUND

1. Field of the Invention

The present invention relates to a catalytic manufacturing method and reaction of an imine having no substituent on a nitrogen, and more particularly, to a method of stably manufacturing imines having no substituent on a nitrogen from an organic azide having α-hydrogen using a suitable metal complex as a catalyst at room temperature under neutral conditions. In addition, the present invention relates to a method of producing various binding products through a reaction between the manufactured imine and an external nucleophile.

2. Discussion of Related Art

The present invention relates to a catalytic method of manufacturing an imine having no substituent on a nitrogen and a reaction of the manufactured imine. It is known that the imine having no substituent on a nitrogen is difficult to be isolated and purified, and particularly, an aldimine having no substituent on a nitrogen is impossibly present in a stable form at room temperature. Meanwhile, some methods of manufacturing an imine having no substituent on a nitrogen have been known. For example, the methods that have been known so far are disclosed in the manufacture through a reaction between oxaziridine and an organic base, DABCO, reported by the Boyd group in 1979 [Boyd, D. R.; Hamilton, R.; Thompson, N. T.; Stubbs, M. E. Tetrahedron Lett., 1979, 20, 3201], allylboration for N-unsubstituted imine generated as an intermediate by reacting water with N-silyl imine reported by the Brown group in 1999 [Chen, G.-M.; Ramachandran, P. V.; Brown, H. C. Angew. Chem. Int. Ed., 1999, 38, 825], allylboration for N-unsubstituted aldimine produced by reacting ammonia to an aldehyde reported by the Kobayashi group in 2004 [Sugiura, M.; Hirano, K.; Kobayashi, S. J. Am. Chem. Soc., 2004, 126, 7182], and allylboration for N-unsubstituted ketimine produced by reacting ammonia to a ketone reported by the Thadani group in 2005 [Dhudshia, B.; Tiburcio, J.; Thadani, A. N. Chem. Commun., 2005, 5551].

However, the above-described examples are all limited to conditions for producing an imine having no substituent on a nitrogen. In synthesis from an oxaziridine, a strong base should be used and fluorenone is generated as a byproduct, and in the Brown method, N-silyl imine should be first synthesized from a reaction between a nitrile and a Grignard reagent. In addition, the method using ammonia should use ammonia at an excessive amount of 20 equivalents or more, and can be applied only to a substrate having no functional group reacting with ammonia, other than aldehyde or ketone. Therefore, a catalytic method of manufacturing an imine having no substituent on various types of nitrogen under mild conditions has not been known until now.

Meanwhile, an organic azide is used as a substrate in various organic reactions capable of forming a new carbon-nitrogen or nitrogen-heteroelement binding. Advantages of the azide compound as a substrate are easiness and diversity of the synthesis, and the azide compound may be synthesized using a halogenated compound, an alcohol, an epoxide, an alkyne, or an amine as a starting material under mild conditions. A reaction using such an organic azide as a reaction material is generally cycloaddition, and some examples of selective decomposition to synthesize a nitrogen-heterocyclic compound have been known. Recently, some examples for equivalent production of a metal-imine complex from an organic azide have been reported [Chiba, S.; Zhang, L.; Lee, J.-Y. J. Am. Chem. Soc. 2010, 132, 7266, Albertina, G.; Antoniuttia, S.; Castro, J. J. Organomet. Chem. 2010, 695, 574], but a catalytic method of manufacturing an imine having no substituent on a nitrogen through selective decomposition of an organic azide has not been known until now.

In addition, since an imine having no substituent on a nitrogen which can stably exist under general conditions has not been known so far, addition of the imine has rarely known, either. Due to such a problem, to obtain an amine adduct that can be obtained through addition, an imine having a substituent on a nitrogen has been used as a starting material. However, such a method has an unavoidable disadvantage of removing a substituent of a nitrogen in the final operation to obtain a necessary amine adduct.

For this reason, a necessity for a method of manufacturing an imine having no substituent on a nitrogen is emphasized.

SUMMARY OF THE INVENTION

The present invention is directed to providing a catalytic method of manufacturing an imine having no substituent on a nitrogen and a method of manufacturing an amine adduct through addition of synthesized imine.

The present invention is also directed to providing a catalytic system which can simply manufacture an imine having no substituent on a nitrogen under neutral conditions from an organic azide having α-hydrogen at high efficiency.

The present invention is also directed to providing a method of obtaining a useful adduct through a reaction with an external nucleophile using the manufactured imine as an intermediate of the reaction.

However, technical objects to be achieved by the present invention are not limited to the above-described objects, and other objects not described above will be clearly understood by those of ordinary skill in the art from the following descriptions.

In one aspect, the present invention provides a method of synthesizing an imine having no substituent on a nitrogen, which includes adding a metal complex to an organic azide.

In one exemplary embodiment of the present invention, the metal complex is a ruthenium complex.

In another exemplary embodiment of the present invention, the ruthenium complex is a ruthenium complex of Formula 1 or Formula 2.

[Formula 1]

[Formula 2]

In Formula 1 or 2, $R_1$ and $R_2$ are each independently hydrogen, substituted or unsubstituted phenyl, or $C_1$~$C_5$ alkyl.

In Formula 1 or 2, FG is a substituent having various functional groups including amino, hydroxyl, amide, ester, and ether.

In still another exemplary embodiment of the present invention, the synthesis is performed through irradiation of visible rays.

In another aspect, the present invention provides a method of manufacturing a binding product through addition of the imine manufactured by the present invention with a nucleophile.

In one exemplary embodiment of the present invention, the binding product is an amine.

In another exemplary embodiment of the present invention, the nucleophile includes an organic metal compound, an organic carbon compound, and an organic heteroelement compound.

BRIEF DESCRIPTION OF THE DRAWINGS

The above and other objects, features, and advantages of the present invention will become more apparent to those of ordinary skill in the art by describing exemplary embodiments thereof in detail with reference to the accompanying drawings, in which.

DETAILED DESCRIPTION OF EXEMPLARY EMBODIMENTS

The inventors conducted research to develop a method of manufacturing various adducts through a reaction between an imine and a nucleophile, and thus developed a method of synthesizing an imine having no substituent on a nitrogen from an organic azide using a metal complex as a catalyst.

As described above, the present invention provides a method of manufacturing various products by providing an imine having no substituent on a nitrogen as a reaction intermediate and reacting the imine with an external nucleophile.

Accordingly, the present invention provides a method of synthesizing an imine having no substituent on a nitrogen, which includes adding a metal complex to an organic azide.

The metal complex may be, but is not limited to, a ruthenium complex.

The ruthenium complex is a ruthenium complex of Formula 1 or Formula 2.

[Formula 1]

[Formula 2]

In Formula 1 or 2, $R_1$ and $R_2$ are each independently hydrogen, substituted or unsubstituted phenyl, or $C_1$~$C_5$ alkyl.

In Formula 1 or 2, FG is a substituent having various functional groups including amino, hydroxyl, amide, ester, and ether.

The ruthenium complex is used as a catalyst of the reaction of producing an imine having no substituent on a nitrogen from an organic azide, and there is no limit to the organic azide used as a starting material of the reaction.

The complex having an amine functional group as an example of the ruthenium complex of Formula 1 may be synthesized by Reaction Formula 2.

<Reaction Formula 2>

<Formula 3>

<Formula 1>

In Reaction Formula 2, the compound of Formula 1 may be manufactured by adding $Ru_3(CO)_{12}$ to the compound of Formula 3 to perform a reaction in an organic solvent such as methanol.

Here, $Ru_3(CO)_{12}$ may be used at 0.31 equivalent based on 1 equivalent of the compound of Formula 3, and the reaction may be performed at 90 to 110° C. for 24 to 48 hours.

The starting material used in the manufacture of the compound of Formula 1 may be manufactured by a conventional method, and when needed, may be a commercially available material.

In addition, as an example of the ruthenium complex represented by Formula 2 according to the present invention, a complex having an amine functional group may be prepared according to a synthesis pathway represented by Reaction Formula 3.

<Reaction Formula 3>

In Reaction Formula 3, $R_1$, $R_2$, and $R_3$ are each independently hydrogen, substituted or unsubstituted phenyl, or $C_{1-5}$ alkyl.

In Reaction Formula 3, the compound of Formula 4 may be manufactured by adding $Ru_3(CO)_{12}$ to the compound of Formula 3 to perform a reaction in an organic solvent such as chloroform.

Here, $Ru_3(CO)_{12}$ may be used at 2 equivalents based on 1 equivalent of the compound of Formula 3, but the present invention is not limited thereto. The reaction may be performed at 90 to 110° C. for 24 to 48 hours, and the temperature and the time are not limited as long as the reaction can easily occur.

The compound of Formula 2 may be manufactured by adding $Na_2CO_3$ as an inorganic base to the compound of Formula 4 manufactured by the above operation to perform a reaction in an organic solvent such as 2-propane alcohol. Here, the used inorganic base may be, but is not limited to, $Na_2CO_3$.

Here, $Na_2CO_3$ may be used at 3 equivalents based on 1 equivalent of the compound of Formula 4, but the present invention is not limited thereto. The reaction may be performed at 90 to 110° C. for 24 to 48 hours, but the present invention is not limited thereto.

Starting materials used to manufacture the compound of Formula 2 may be manufactured by a conventional method, and when needed, a commercially available material.

The ruthenium complexes represented by Formulas 1 and 2 of the present invention manufactured by the above-described method may be used as a catalyst for a reaction of synthesizing an imine having no substituent on a nitrogen from an organic azide having α-hydrogen.

Figure 1:
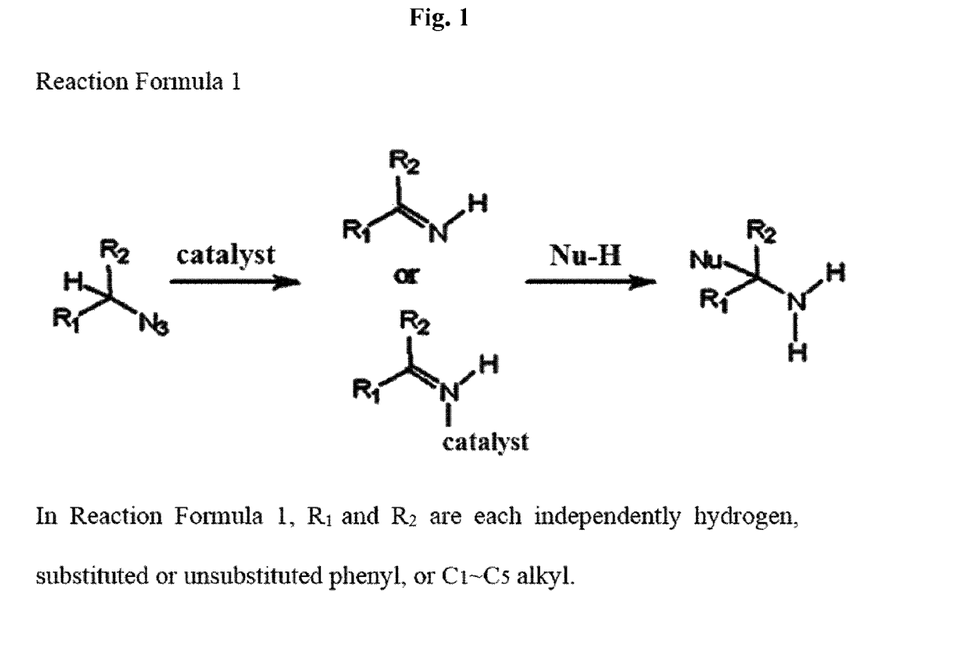
FIG. 1 shows a reaction formula of synthesizing an imine having no substituent on a nitrogen using a metal complex as a catalyst.

More particularly, as shown in Reaction Formula 1 of FIG. 1, the imine having no substituent on a nitrogen may be synthesized by adding the ruthenium complex to the organic azide having α-hydrogen through irradiation of visible rays. The imine having no substituent on a nitrogen produced thereby may react with a nucleophile to synthesize various binding products. Here, the irradiation of the visible rays may be performed using a 30 W home fluorescent lamp as described in the exemplary embodiment of the present invention, but any device for irradiating the visible rays may be used without limitation. The synthesis of the imine having no substituent on a nitrogen may be performed in an inert gas at room temperature for a suitable time.

The nucleophile may be, but is not limited to, an organic metal compound, an organic carbon compound, or an organic heteroelement compound. The organic metal compound may be a Grignard reagent, a Gilman reagent, or a boron reagent, the organic carbon compound may be an enolate, an active methylene compound, or a diazo compound, and the organic heteroelement compound may be an amine or an alcohol. As the imine, any compound capable of serving as a nucleophile may be used without limitation, and preferably, as shown in the exemplary embodiment of the present invention, the organic carbon compound or the organic heteroelement compound may be used.

In one exemplary embodiment of the present invention, the imine having no substituent on a nitrogen may be manufactured by reacting the organic azide with the compound of Formula 1 (refer to Example 1). The organic azide may be the aromatic or aliphatic azide, and an example using benzyl azide is shown in Reaction Formula 4.

<Reaction Formula 4>

Specifically, the ruthenium complex of the present invention may be used as a catalyst for coupling an organic azide having α-hydrogen and an amine in the use of a 30 W home fluorescent lamp irradiating visible rays.

In addition, as shown in Reaction Formula 4, the synthesis reaction of an imine having a substituent on a nitrogen through the coupling of the azide and the amine may be performed in an inert gas at room temperature for a suitable time. A ratio of the azide and the amine used in the reaction may vary, and preferably, 1:1.2. An organic solvent used in the reaction may be, tetrahydrofuran, toluene, benzene, or ethylacetate, and preferably, tetrahydrofuran, and the reaction temperature is preferably room temperature. While changed according to a type of the amine, a ruthenium catalytic amount used in the reaction may be 1 to 3 mol %, and preferably 1 mol %.

In another exemplary embodiment of the present invention, an imine having a substituent on a nitrogen was manufactured by coupling an organic azide and an amine with the ruthenium complex of the present invention, and compared with the imine having no substituent on a nitrogen of the present invention (refer to Example 2). An example using benzyl azide and an organic heteroelement compound, that is, hexylamine as an amine is shown in Reaction Formula 5.

<Reaction Formula 5>

>95%

In Reaction Formula 5, an imine is formed by a reaction of benzyl azide and the compound of Formula 1, and reacted with an amine as a nucleophile, thereby forming an imine having a substituent on a nitrogen.

In the imine having a substituent on a nitrogen shown in Reaction Formula 5, the substituent (—X) should onerously be removed after reacting with a nucleophile as shown in the following reaction formula. However, it is advantageous that the imine having no substituent on a nitrogen formed by the method of the present invention may react with a nucleophile, thereby directly obtaining a synthetic material.

<Reaction Formula>

N-unsubstituted imines

In addition, the ruthenium complex of the present invention may be used as a catalyst in the addition of an imine manufactured from an organic azide having α-hydrogen and an organic metal compound, that is, an allyl boron compound (refer to Example 3). Synthesis of a homo allyl amine by addition of the imine manufactured from an organic azide having α-hydrogen and the allyl boron compound may be performed in an inert gas from −78° C. to room temperature for a suitable time.

A ratio of the azide and the allyl boron compound used in the reaction may vary, and preferably 1:1.5. The organic solvent used in the reaction may be tetrahydrofuran, toluene, benzene, or ethylacetate, and preferably, tetrahydrofuran, and the reaction temperature is preferably room temperature. While changed according to a type of the azide, a ruthenium catalytic amount used in the reaction may be 1 to 3 mol %, and preferably 1 mol %. An example of reacting the benzyl azide and the allyl boron compound, that is, allylboronic acid pinacol ester is shown in Reaction Formula 6.

<Reaction Formula 6>

83%

In Reaction Formula 6, the imine having no substituent on a nitrogen is formed by reacting the benzyl azide and the compound of Formula 1, and the organic carbon compound, allylboronic acid pinacol ester, acts as a nucleophile, thereby obtaining a product.

In still another exemplary embodiment of the present invention, it was confirmed that a ruthenium complex can be used as a catalyst for diastereoselective addition between an imine produced from an organic azide having α-hydrogen and an allyl boron compound using a 30 W home fluorescent lamp irradiating visible rays (refer to Example 4). As such, synthesis of a homo allyl amine by the diastereoselective addition between the imine produced from the organic azide having α-hydrogen and the allyl boron compound may be performed in an inert gas until room temperature for a suitable time.

A ratio of the azide and the allyl boron compound used in the diastereoselective reaction of the present invention may vary, and preferably 1:1.5. The organic solvent used in the reaction may be tetrahydrofuran, toluene, benzene, or ethylacetate, and preferably, tetrahydrofuran, and the reaction temperature is preferably room temperature. While changed according to a type of the azide, a ruthenium catalytic amount used in the reaction may be 1 to 3 mol %, and preferably 1 mol %. An example of reacting the benzyl azide and an allyl boron compound, that is, trans-crotylboronic acid pinacol ester or cis-crotylboronic acid pinacol ester is shown in Reaction Formula 7.

<Reaction Formula 7>

From Reaction Formula 7, it can be confirmed that a diastereoselective product can be obtained by a reaction between the imine having no substituent on a nitrogen formed by the method of the present invention and the allyl boron compound.

In addition, in yet another exemplary embodiment of the present invention, it was confirmed that a ruthenium complex can be used as a catalyst for asymmetric addition between an imine produced from an organic azide having α-hydrogen and an allyl boron compound using a 30 W home fluorescent lamp irradiating visible rays (refer to Example 5). As such, synthesis of a homo allyl amine by the asymmetric addition between the imine produced from the organic azide having α-hydrogen and the allyl boron compound may be performed in an inert gas at −78° C. for a suitable time.

A ratio of the azide and the allyl boron compound used in the asymmetric reaction may vary, and preferably, 1:15. The organic solvent used in the reaction may be tetrahydrofuran, toluene, benzene, or ethylacetate, and preferably, tetrahydrofuran, and the reaction temperature is preferably −78° C. While changed according to a type of the azide, a ruthenium catalytic amount used in the reaction may be 1 to 3 mol %, and preferably 2.5 mol %.

An example of reacting benzyl azide as the aromatic or aliphatic azide and (−)-Ipc$_2$B(allyl)borane as the allyl boron compound is shown in Reaction Formula 8.

<Reaction Formula 8>

Through Reaction Formulas 5 to 8, it was confirmed that the imine having no substituent on a nitrogen synthesized by the method of the present invention can be utilized as a useful intermediate in various syntheses.

Hereinafter, exemplary examples will be provided to help in understanding the present invention. However, the following examples are provided to more easily understand the present invention, but the scope of the present invention is not limited to the following examples.

EXAMPLES

Example 1

Manufacture of Imine Having No Substituent on Nitrogen from Azide

In this example, an imine having no substituent on a nitrogen was manufactured using a ruthenium complex of the present invention.

A compound of Formula 1 (4.6 mg, 0.005 mmol) and benzyl azide (66.6 mg, 0.50 mmol) were dissolved in 0.5 ml of tetrahydrofuran-d$_8$, and stirred for 10 hours under irradiation of a 30 W home fluorescent lamp at room temperature in an argon gas. After the reaction was completed, a corresponding imine was obtained with an yield of 95%.

In Example 1, it was confirmed that the imine having no substituent on a nitrogen can be manufactured using the compound of Formula 1, that is, the ruthenium complex.

Reaction Formula 1 according to Example 1 is shown in FIG. 1.

Example 2

Manufacture of Imine Having Substituent on Nitrogen Through Coupling Between Azide and Amine In this example, an imine having a substituent on a nitrogen was manufactured by coupling an azide and an amine as a conventional imine synthesis reaction.

<2-1>

The compound of Formula 1 manufactured as described above (4.6 mg, 0.005 mmol), benzyl azide (66.6 mg, 0.50 mmol), and n-hexylamine (79 µl, 0.60 mmol) were dissolved in 1.0 ml of tetrahydrofuran, and stirred for 3 hours under irradiation of a 30 W home fluorescent lamp at room temperature in an argon gas. After the reaction was completed, a corresponding imine was obtained with an yield of 95%.

<2-2>

The compound of Formula 1 manufactured as described above (4.6 mg, 0.005 mmol), benzyl azide (66.6 mg, 0.50 mmol), and cyclohexylamine (86 µl, 0.75 mmol) were dissolved in 1.0 ml of tetrahydrofuran, and stirred for 3 hours under irradiation of a 30 W home fluorescent lamp at room temperature in an argon gas. After the reaction was completed, a corresponding imine was obtained with an yield of 97%.

<2-3>

The compound of Formula 1 manufactured as described above (4.6 mg, 0.005 mmol), benzyl azide (66.6 mg, 0.50 mmol), and tert-butylamine (79 µl, 0.75 mmol) were dissolved in 1.0 ml of tetrahydrofuran, and stirred for 3 hours under irradiation of a 30 W home fluorescent lamp at room temperature in an argon gas. After the reaction was completed, a corresponding imine was obtained with an yield of 48%.

<2-4>

The compound of Formula 1 manufactured as described above (4.6 mg, 0.005 mmol), benzyl azide (66.6 mg, 0.50 mmol), and arylamine (56 µl, 0.75 mmol) were dissolved in 1.0 ml of tetrahydrofuran, and stirred for 22 hours under irradiation of a 30 W home fluorescent lamp at room temperature in an argon gas. After the reaction was completed, a corresponding imine was obtained with an yield of 99%.

<2-5>

The compound of Formula 1 manufactured as described above (4.6 mg, 0.005 mmol), benzyl azide (66.6 mg, 0.50 mmol), and pentane-1,3-diamine (72 µl, 0.60 mmol) were dissolved in 1.0 ml of tetrahydrofuran, and stirred for 3 hours under irradiation of a 30 W home fluorescent lamp at room temperature in an argon gas. After the reaction was completed, a corresponding imine was obtained with an yield of 89%.

$^1$H NMR (300 MHz, CDCl$_3$) δ ppm 7.49-7.46 (m, 2H), 7.34-7.24 (m, 3H), 4.54 (s, 1H), 3.30-3.24 (m, 1H), 2.93 (td, J(H,H)=12.8 Hz, J(H,H)=3.2 Hz, 1H), 2.77-2.73 (m, 1H), 1.67-1.60 (m, 1H), 1.48-1.39 (m, 2H), 1.26-1.17 (m, 1H), 0.93 (t, J(H,H)=7.5 Hz, 3H); $^{13}$C NMR (75 MHz, CDCl$_3$) δppm 142.9, 128.5, 128.0, 126.5, 75.0, 58.0. 46.4, 32.9, 30.2, 10.1

<2-6>

The compound of Formula 1 manufactured as described above (4.6 mg, 0.005 mmol), benzyl azide (66.6 mg, 0.50 mmol), and benzylamine (66 µl, 0.60 mmol) were dissolved in 1.0 ml of tetrahydrofuran, and stirred for 3 hours under irradiation of a 30 W home fluorescent lamp at room temperature in an argon gas. After the reaction was completed, the corresponding imine was obtained with an yield of 95%.

<2-7>

The compound of Formula 1 manufactured as described above (4.6 mg, 0.005 mmol), benzyl azide (66.6 mg, 0.50 mmol), and 2-picolylamine (62 µl, 0.60 mmol) were dissolved in 1.0 ml of tetrahydrofuran, and stirred for 3 hours under irradiation of a 30 W home fluorescent lamp at room temperature in an argon gas. After the reaction was completed, a corresponding imine was obtained with an yield of 86%.

<2-8>

The compound of Formula 1 manufactured as described above (4.6 mg, 0.005 mmol), 1-azidomethyl-4-methoxybenzene (81.5 mg, 0.50 mmol), and n-hexylamine (79 µl, 0.60 mmol) were dissolved in 1.0 ml of tetrahydrofuran, and stirred for 3 hours under irradiation of a 30 W home fluorescent lamp at room temperature in an argon gas. After the reaction was completed, a corresponding imine was obtained with an yield of 87%.

<2-9>

The compound of Formula 1 manufactured as described above (9.2 mg, 0.010 mmol), 4-azidomethylbenzonitrile (79.1 mg, 0.50 mmol), and n-hexylamine (99 µl, 0.75 mmol) were dissolved in 1.0 ml of tetrahydrofuran, and stirred for 3 hours under irradiation of a 30 W home fluorescent lamp at room temperature in an argon gas. After the reaction was completed, a corresponding imine was obtained with an yield of 60%.

$^1$H NMR (300 MHz, CDCl$_3$) δppm 8.30 (s, 1H), 7.85-7.80 (m, 2H), 7.70-7.67 (m, 2H), 3.65 (td, J(H,H)=7.0 Hz, J(H,H)=1.3 Hz, 2H), 1.72-1.68 (m, 2H), 1.39-1.29 (m, 6H), 0.91-0.87 (m, 3H); $^{13}$C NMR (75 MHz, CDCl$_3$) δppm 158.9, 140.3, 132.5, 128.5, 118.7, 113.7, 62.0, 31.7, 30.8, 27.1, 22.7, 14.1

<2-10>

The compound of Formula 1 manufactured as described above (9.2 mg, 0.010 mmol), 4-azidomethylbromobenzene (106 mg, 0.50 mmol), and n-hexylamine (99 µl, 0.75 mmol) were dissolved in 1.0 ml of tetrahydrofuran, and stirred for 3 hours under irradiation of a 30 W home fluorescent lamp at room temperature in an argon gas. After the reaction was completed, a corresponding imine was obtained with an yield of 98%.

$^1$H NMR (300 MHz, CDCl$_3$) δppm 8.20 (s, 1H), 7.59-7.50 (m, 4H), 3.60 (td, J(H,H)=7.0 Hz, J(H,H)=1.2 Hz, 2H), 1.70-1.63 (m, 2H), 1.37-1.26 (m, 6H), 0.91-0.67 (m, 3H); $^{13}$C NMR (75 MHz, CDCl$_3$) δppm 159.5, 135.4, 131.9, 129.6, 124.9, 61.9, 31.8, 31.0, 27.2, 22.8, 14.2

<2-11>

The compound of Formula 1 manufactured as described above (9.2 mg, 0.010 mmol), 2-azidoethylbenzene (73.6 mg, 0.50 mmol), and n-hexylamine (99 µl, 0.75 mmol) were dissolved in 1.0 ml of tetrahydrofuran, and stirred for 3 hours under irradiation of a 30 W home fluorescent lamp at room temperature in an argon gas. After the reaction was completed, a corresponding imine was obtained with an yield of 69%.

$^1$H NMR (300 MHz, CDCl$_3$) δppm 7.68 (tt, J(H,H)=5.2 Hz, J(H,H)=1.3 Hz, 1H), 7.32-7.15 (m, 5H), 3.57 (d, J(H,H)=5.2 Hz, 2H), 3.37 (t, J(H,H)=7.1 Hz, 2H), 1.61-1.58 (m, 2H), 1.28 (m, 6H), 0.90-0.85 (m, 3H); $^{13}$C NMR (75 MHz, CDCl$_3$) δppm 162.8, 136.8, 129.2, 128.8, 126.8, 61.4, 42.9, 31.7, 30.8, 27.0, 22.7, 14.2

<2-12>

The compound of Formula 1 manufactured as described above (4.6 mg, 0.005 mmol), 1-azidooctane (77.6 mg, 0.50 mmol), and n-hexylamine (79 µl, 0.60 mmol) were dissolved in 1.0 ml of tetrahydrofuran, and stirred for 3 hours under irradiation of a 30 W home fluorescent lamp at room temperature in an argon gas. After the reaction was completed, a corresponding imine was obtained with an yield of 96%.

$^1$H NMR (300 MHz, CDCl$_3$) δppm 7.62 (t, J(H,H)=4.9 Hz, 1H), 3.34 (t, J(H,H)=7.0 Hz, 2H), 2.26-2.19 (m, 2H), 1.60-1.49 (m, 4H), 1.29 (m, 14H), 0.90-0.86 (m, 6H); $^{13}$C NMR (75 MHz, CDCl$_3$) δppm 164.9, 61.6, 36.0, 31.9, 31.8, 30.9, 29.4, 29.2, 27.0, 26.3, 22.8, 14.2

<2-13>

The compound of Formula 1 manufactured as described above (9.2 mg, 0.010 mmol), 1-azidooctane (77.6 mg, 0.50 mmol), and benzylamine (83 µl, 0.75 mmol) were dissolved in 1.0 ml of tetrahydrofuran, and stirred for 3 hours under irradiation of a 30 W home fluorescent lamp at room temperature in an argon gas. After the reaction was completed, a corresponding imine was obtained with an yield of 92%.

<2-14>

The compound of Formula 1 manufactured as described above (4.6 mg, 0.005 mmol), azidocyclohexane (62.6 mg, 0.50 mmol), and n-hexylamine (99 μl, 0.75 mmol) were dissolved in 1.0 ml of tetrahydrofuran, and stirred for 3 hours under irradiation of a 30 W home fluorescent lamp at room temperature in an argon gas. After the reaction was completed, the corresponding imine was obtained with an yield of 82%.

$^1$H NMR (300 MHz, CDCl$_3$) δppm 3.29 (t, J(H,H)=7.3 Hz, 2H), 2.23 (m, 4H), 1.72-1.59 (m, 8H), 1.30 (m, 6H), 0.89-0.86 (m, 3H); $^{13}$C NMR (75 MHz, CDCl$_3$) δppm 172.7, 50.5, 40.2, 31.9, 31.3, 28.9, 27.9, 27.4, 27.2, 26.3, 22.8, 14.2

Figure 2:
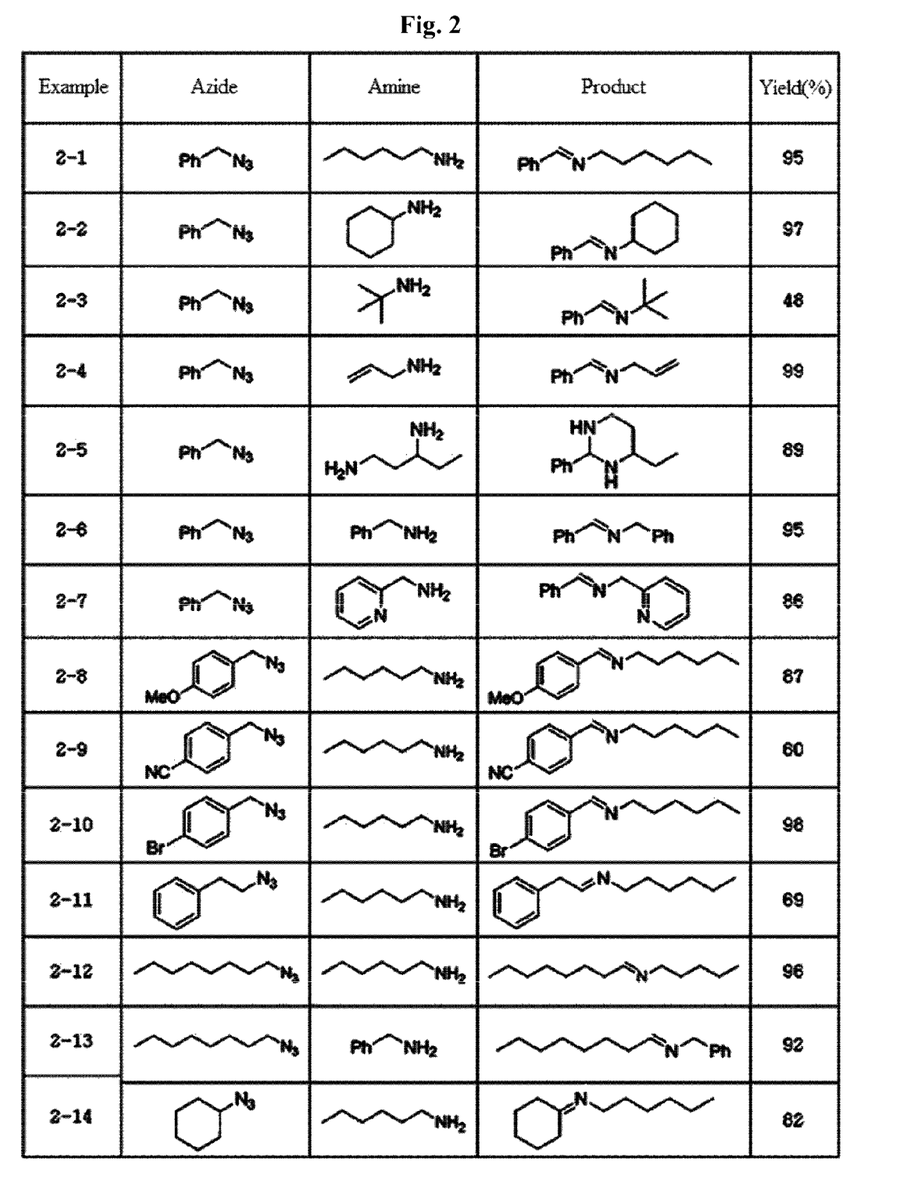
FIG. 2 is a table showing an imine compound having a substituent on a nitrogen which is synthesized by coupling an organic azide and an amine using a metal complex as a catalyst and an yield thereof.

The products synthesized according to Example 2 and their yields are shown in FIG. 2. Referring to FIG. 2, it can be confirmed that the compound of Formula 1, that is, the ruthenium complex of the present invention, was used as a catalyst for coupling an amine and azide, thereby synthesizing an amine adduct. The imines formed in Example 2 are imines having a substituent on a nitrogen as used in the conventional research method. The imines formed as described above have a disadvantage of additionally removing a substituent in a further reaction with organic compounds.

Therefore, a method of synthesizing an imine having no substituent on a nitrogen in a different way from that used in Example 2 for synthesizing an imine having a substituent on a nitrogen has an advantage of directly reacting with an organic compound.

Accordingly as an example, Examples 3 to 5 were performed to examine that a new product can be synthesized by reacting the imine having no substituent on a nitrogen produced by the method of Example 1 with various organic compounds, as an intermediate. Here, the organic compounds act as a nucleophile.

Example 3

Addition Between Imine Having No Substituent on Nitrogen Produced from Organic Azide Having α-Hydrogen and Allyl Boron Compound In this example, addition between an imine having no substituent on a nitrogen produced from an organic azide having α-hydrogen and an allyl boron compound was performed using a compound of Formula 1, that is, a ruthenium complex.

<3-1>

The compound of Formula 1 manufactured as described above (4.8 mg, 0.005 mmol), benzyl azide (66.6 mg, 0.50 mmol), and allylboronic acid pinacol ester (144 μl, 0.75 mmol) were dissolved in 0.50 ml of tetrahydrofuran, and stirred for 3 hours under irradiation of a 30 W home fluorescent lamp at room temperature in an argon gas. After the reaction was completed, a solvent was removed, and the resulting product was isolated and purified, thereby obtaining a corresponding homo allyl amine with an yield of 83%.

$^1$H NMR (300 MHz, CDCl$_3$) δppm 7.18-7.40 (m, 5H), 5.76 (dddd, J=17.1, 10.2, 8.0, 6.5 Hz, 1H), 5.05-5.16 (m, 2H), 4.00 (dd, J=8.1, 5.1 Hz, 1H), 2.30-2.54 (m, 2H), 1.52 (br s, 2H); $^{13}$C NMR (75 MHz, CDCl$_3$) δppm 146.1, 135.7, 128.6, 127.2, 126.5, 117.8, 55.6, 44.4

<3-2>

The compound of Formula 1 manufactured as described above (4.8 mg, 0.005 mmol), 1-azidooctane (77.6 mg, 0.50 mmol), and allylboronic acid pinacol ester (144 μl, 0.75 mmol) were dissolved in 0.50 ml of tetrahydrofuran, and stirred for 3 hours under irradiation of a 30 W home fluorescent lamp at room temperature in an argon gas. After the reaction was completed, a solvent was removed, and the resulting product was isolated and purified, thereby obtaining a corresponding homo allyl amine with an yield of 85%.

$^1$H NMR (300 MHz, CDCl$_3$) δppm 5.79 (dddd, J=16.5, 10.0, 8.0, 2.2 Hz 1H), 5.02-5.14 (m, 2H), 2.68-2.84 (m, 1H), 2.17-2.28 (m, 1H), 1.96 (dt, J=13.8, 8.1 Hz, 1H), 1.17-1.43 (m, 14H), 0.87 (t, J=6.6 Hz, 3H); $^{13}$C NMR (75 MHz, CDCl$_3$) δppm 136.2, 117.4, 50.8, 42.9, 38.0, 32.1, 29.9, 29.5, 26.5, 22.9, 14.3

<3-3>

The compound of Formula 1 manufactured as described above (4.8 mg, 0.005 mmol), methyl 4-(azidomethyl)benzoate (95.6 mg, 0.50 mmol), and allylboronic acid pinacol ester (144 μl, 0.75 mmol) were dissolved in 0.50 ml of tetrahydrofuran, and stirred for 3 hours under irradiation of a 30 W home fluorescent lamp at room temperature in an argon gas. After the reaction was completed, a solvent was removed, and the resulting product was isolated and purified, thereby obtaining a corresponding homo allyl amine with an yield of 91%.

$^1$H NMR (300 MHz, CDCl$_3$) δppm 8.00 (dd, J=6.6, 1.8 Hz, 2H), 7.42 (d, J=8.4 Hz, 2H), 5.26 (dddd, J=16.7, 10.4, 8.0, 6.5 Hz, 1H), 5.07-5.16 (m, 2H), 4.07 (dd, J=7.8, 5.4 Hz, 1H), 3.91 (s, 3H), 2.29-2.52 (m, 2H), 1.56 (br s, 2H); $^{13}$C NMR (75 MHz, CDCl$_3$) δppm 167.2, 151.2, 135.0, 130.0, 129.1, 126.6, 118.3, 55.4, 52.2, 44.2

IR (cm$^{-1}$) v 3074, 2952, 1721, 1640, 1611, 1436, 1417, 1310, 1280, 1180, 1113, 1019, 918, 856

LR FAB Mass: m/z 206.1181 (M+H), m/z 206.1182 (M+Na)

<3-4>

The compound of Formula 1 manufactured as described above (5.1 mg, 0.005 mmol), ethyl-2-azidoacetate (64.6 mg, 0.50 mmol), and allylboronic acid pinacol ester (144 μl, 0.75 mmol) were dissolved in 0.50 ml of tetrahydrofuran, and stirred for 3 hours under irradiation of a 30 W home fluorescent lamp at room temperature in an argon gas. After the reaction was completed, a solvent was removed, and the resulting product was isolated and purified, thereby obtaining a corresponding homo allyl amine with an yield of 73%.

$^1$H NMR (300 MHz, CDCl$_3$) δppm 5.75 (ddt, J=16.8, 10.2, 7.2 Hz, 1H), 5.07-5.24 (m, 2H), 4.10-4.28 (m, 2H), 3.53 (dd, J=7.2, 5.4 Hz, 1H), 2.45-2.58 (m, 1H), 2.31-2.45 (m, 1H), 1.63 (br s, 2H), 1.28 (t, J=7.2 Hz, 3H); $^{13}$C NMR (75 MHz, CDCl$_3$) δppm 175.2, 133.5, 118, 61.2, 54.0, 39.2, 14.4

<3-5>

The compound of Formula 1 manufactured as described above (4.6 mg, 0.0045 mmol), azidocyclohexane (28.4 mg, 0.227 mmol), and allylboronic acid pinacol ester (66 μl, 0.341 mmol) were dissolved in 0.50 ml of tetrahydrofuran, and stirred for 3 hours under irradiation of a 30 W home fluorescent lamp at room temperature in an argon gas. After the reaction was completed, a solvent was removed, and the resulting product was isolated and purified, thereby obtaining a corresponding homo allyl amine with an yield of 69%.

$^1$H NMR (300 MHz, CDCl$_3$) δppm 5.86 (ddt, J=16.7, 10.4, 7.5 Hz, 1H), 5.05-5.16 (m, 2H), 2.13 (d, J=7.5 Hz, 2H), 1.25-1.63 (m, 12H); $^{13}$C NMR (75 MHz, CDCl$_3$) δppm 134.3, 118.4, 51.0, 47.0, 38.7, 26.1, 22.4

<3-6>

Figure 3:
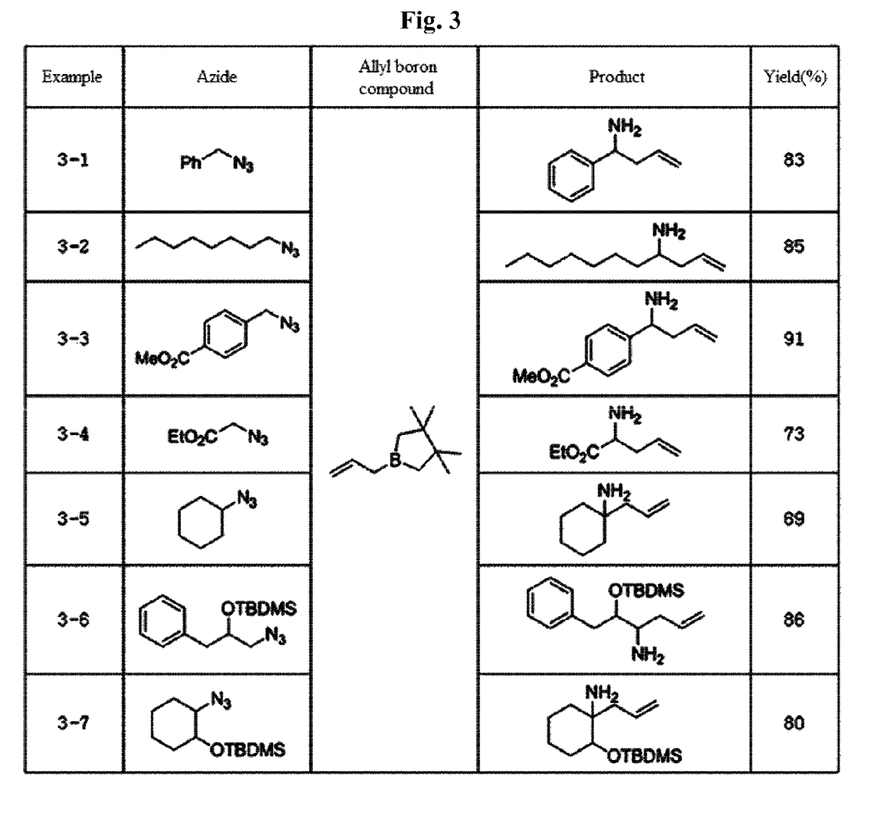
FIG. 3 is a table showing an amine compound synthesized through addition between an imine having no substituent on a nitrogen produced using a ruthenium complex, which is one of metal complexes, as a catalyst and an allyl boron compound, and an yield thereof.

The compound of Formula 1 manufactured as described above (2.6 mg, 0.005 mmol), (1-azido-3-phenylpropan-2-yloxy)(tert-butyl)dimethylsilane (72.9 mg, 0.250 mmol), and allylboronic acid pinacol ester (72.5 µl, 0.375 mmol) were dissolved in 0.50 ml of tetrahydrofuran, and stirred for 3 hours under irradiation of a 30 W home fluorescent lamp at −15° C. in an argon gas. After the reaction was completed, a solvent was removed, and the resulting product was isolated and purified, thereby obtaining a corresponding homo allyl amine with an yield of 86%. In FIG. 3, TBDMS means tert-butyldimethylsilyl.

$^1$H NMR (300 MHz, CDCl$_3$) δppm 7.31-7.42 (m, 2H), 7.19-7.30 (m, 3H), 5.68-5.97 (m, 1H), 5.00-5.24 (m, 2H), 3.78-3.94 (m, 1H), 3.02 (dd, J=13.4, 7.1 Hz, 0.87H), 2.89-2.95 (m, 0.13H), 2.71-2.85 (m, 1.13H), 2.58-2.67 (m, 0.87H), 2.26-2.39 (m, 1H), 2.13-2.23 (m, 0.13H), 2.06 (dt, J=13.8, 8.4 Hz, 0.87H), 1.23-1.39 (m, 2H), 0.94 (s, 7.83H), 0.88 (s, 1.17H), 0.07 (s, 2.61H), −0.04 (s, 0.39H), −0.09 (s, 2.61H), −0.35 (s, 0.39H); $^{13}$C NMR (75 MHz, CDCl$_3$) δppm 139.5, 139.1, 136.6, 136.2, 130.0, 129.8, 128.5, 128.3, 126.3, 126.2, 117.3, 117.1, 76.7, 55.2, 53.3, 40.3, 39.8, 38.0, 37.9, 26.1, 26.0, 18.3, −4.4, −4.6, −5.1

<3-7>

The compound of Formula 1 manufactured as described above (10.2 mg, 0.01 mmol), (2-azidocyclohexyloxy)(tert-butyl)dimethylsilane (127.7 mg, 0.500 mmol), and allylboronic acid pinacol ester (144 µl, 0.750 mmol) were dissolved in 0.50 ml of tetrahydrofuran, and stirred for 3 hours under irradiation of a 30 W home fluorescent lamp at room temperature in an argon gas. After the reaction was completed, a solvent was removed, and the resulting product was isolated and purified, thereby obtaining a corresponding homo allyl amine with an yield of 80%.

$^1$H NMR (300 MHz, CDCl$_3$) δppm 5.85 (ddd, J=24.3, 9.9, 7.5 Hz, 1H), 4.96-5.15 (m, 2H), 3.41 (dd, J=8.9, 4.1 Hz, 1H), 2.30 (dd, J=13.5, 7.2 Hz, 1H), 2.12 (dd, J=13.5, 7.8 Hz, 1H), 1.54-1.66 (m, 4H), 1.39-1.47 (m, 2H), 1.19-1.30 (m, 4H), 0.90 (s, 9H), 0.06 (s, 6H); $^{13}$C NMR (75 MHz, CDCl$_3$) δppm 134.7, 118.0, 75.6, 54.7, 45.1, 34.7, 30.8, 26.1, 25.1, 23.5, 21.3, 18.3, −3.6, −4.6

IR (cm$^{-1}$) v 3075, 2930, 2857, 1638, 1472, 1463, 1361, 1250, 1090, 1050, 1022

LR FAB Mass: m/z 269.2175 (M+H), m/z 269.2178 (M+Na)

The products synthesized according to Example 3 and their yields are shown in FIG. 3. Referring to FIG. 3, it can be confirmed that the compound of Formula 1, that is, the ruthenium complex of the present invention, was used as a catalyst to easily perform addition between the imine having no substituent on a nitrogen produced from the organic azide having α-hydrogen and the allyl boron compound.

Example 4

Diastereoselective Addition Between Imine Produced from Organic Azide Having α-Hydrogen and Allyl Boron Compound In this example, diastereoselective addition between an imine having no substituent on a nitrogen produced from an organic azide having α-hydrogen and an allyl boron compound was performed using a ruthenium complex of the present invention as a catalyst.

<4-1>

The compound of Formula 1 manufactured as described above (5.1 mg, 0.005 mmol), benzyl azide (66.6 mg, 0.50 mmol), and trans-crotylboronic acid pinacol ester (137 mg, 0.75 mmol) were dissolved in 0.50 ml of tetrahydrofuran, and stirred for 3 hours under irradiation of a 30 W home fluorescent lamp at room temperature in an argon gas. After the reaction was completed, a solvent was removed, and the resulting product was isolated and purified, thereby obtaining a corresponding homo allyl amine with an yield of 71%.

$^1$H NMR (300 MHz, CDCl$_3$) δppm 7.20-7.38 (m, 5H), 5.75 (ddd, J=17.1, 10.2, 8.4 Hz, 1H), 5.05-5.22 (m, 2H), 3.64 (J=8.4 Hz, 1H), 2.30-2.44 (m, 1H), 1.52 (br s, 2H), 0.82 (d, J=6.9 Hz, 3H); $^{13}$C NMR (75 MHz, CDCl$_3$) δppm 144.8, 141.9, 128.5, 127.5, 127.3, 116.0, 60.9, 46.6, 17.9

<4-2>

The compound of Formula 1 manufactured as described above (2.6 mg, 0.0025 mmol), benzyl azide (33.3 mg, 0.25 mmol), and cis-crotylboronic acid pinacol ester (68.3 mg, 0.375 mmol) were dissolved in 0.50 ml of tetrahydrofuran, and stirred for 3 hours under irradiation of a 30 W home fluorescent lamp at room temperature in an argon gas. After the reaction was completed, a solvent was removed, and the resulting product was isolated and purified, thereby obtaining a corresponding homo allyl amine with an yield of 80%.

$^1$H NMR (300 MHz, CDCl$_3$) δppm 7.19-7.40 (m, 5H), 5.75 (ddd, J=17.3, 9.8, 7.6 Hz, 1H), 4.97-5.12 (m, 2H), 3.89 (d, J=5.4 Hz, 1H), 2.44-2.60 (m, 1H), 1.65 (br s, 2H), 0.98 (d, J=6.9 Hz, 3H); $^{13}$C NMR (75 MHz, CDCl$_3$) δppm 144.5, 141.2, 128.2, 127.4, 127.0, 115.3, 60.2, 44.9, 15.3

According to this example, it was confirmed that the amine compound is produced with a high yield through the diastereoselective addition between the imine having no substituent on a nitrogen produced from the organic azide and the allyl boron compound.

Figure 4:
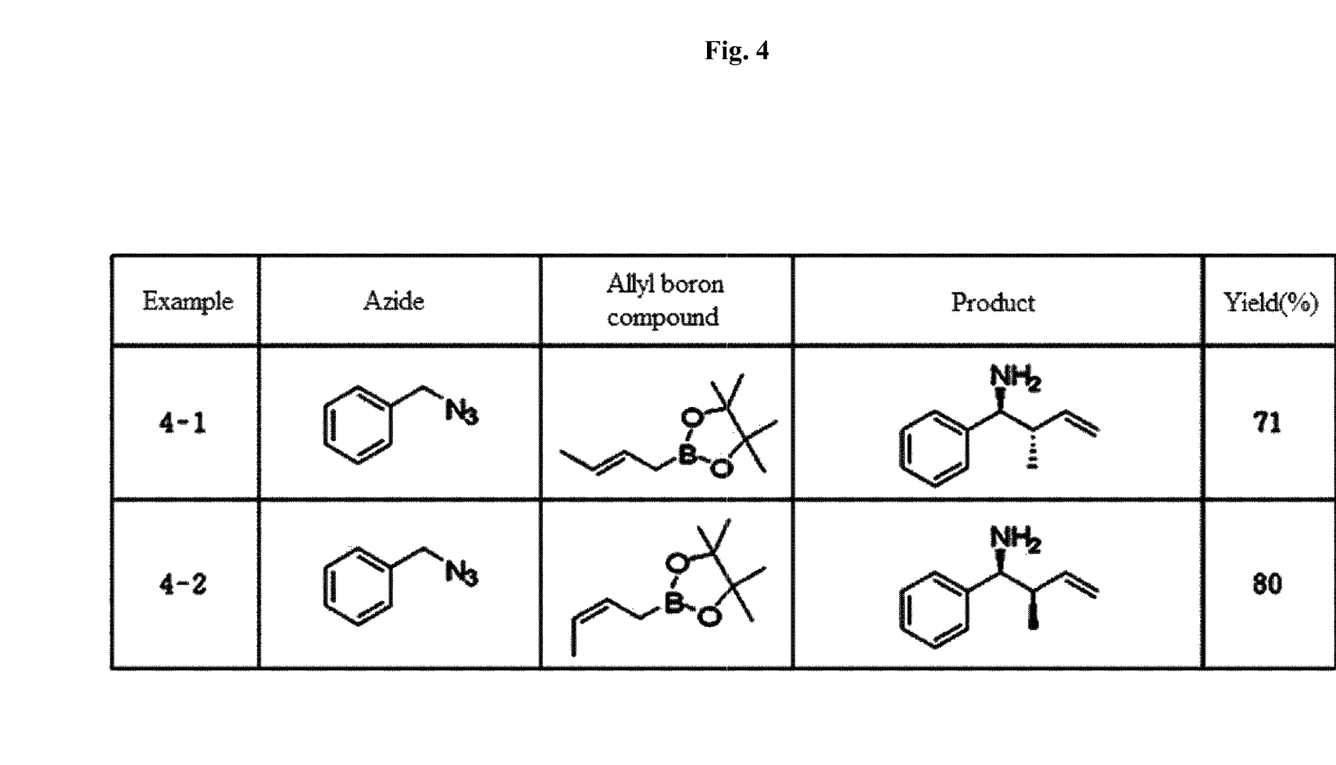
FIG. 4 is a table showing an amine compound synthesized through diastereoselective addition between an imine having no substituent on a nitrogen produced using a ruthenium complex, which is one of metal complexes, as a catalyst and an allyl boron compound, and an yield thereof.

The compound produced in Example 4 and its yield are shown in FIG. 4.

Example 5

Asymmetric Addition Between Imine Produced from Organic Azide Having α-Hydrogen and Allyl Boron Compound In this example, diastereoselective addition between an imine having no substituent on a nitrogen produced from an organic azide having α-hydrogen and an allyl boron compound was performed using a ruthenium complex of the present invention as a catalyst.

<5-1>

The compound of Formula 1 manufactured as described above (6.4 mg, 0.0063 mmol), benzyl azide (33.3 mg, 0.25 mmol), and (−)-Ipc$_2$B(allyl)borane (0.375 mL, 0.375 mmol, 1M in pentane) were dissolved in 0.50 ml of tetrahydrofuran, and stirred for 3 hours under irradiation of a 30 W home fluorescent lamp at room temperature in an argon gas. After the reaction was completed, a solvent was removed, and the resulting product was isolated and purified, thereby obtaining a corresponding homo allyl amine with an yield of 87% and an optical purity of 89%.

According to Example 5, it was confirmed that the imine having no substituent on a nitrogen is synthesized from the organic azide having α-hydrogen using the ruthenium complex of the present invention as a catalyst, and then the amine compound can be obtained from the synthesized imine with a high yield.

From Examples 2 to 5, it was confirmed that various compounds including an amine compound can be manufactured through addition between the imine having no substituent on a nitrogen manufactured by the method of the present invention and various compounds. It provides that the imine having no substituent on a nitrogen manufactured by the method of the present invention can be used as a useful intermediate in various types of organic synthesis reactions.

According to the present invention, a process of manufacturing an imine having no substituent on a nitrogen and a process of reacting the produced imine and an external nucleophile are provided.

The process of manufacturing an imine having no substituent on a nitrogen according to the present invention provides a process of efficiently and simply manufacturing an imine having no substituent on a nitrogen under neutral conditions, which has not been known yet. Therefore, various applications can be provided.

The imine having no substituent on a nitrogen provided by the present invention can manufacture various binding products through a reaction with the external nucleophile. The binding products produced by the method can be used as a useful compound in various fields including pharmaceuticals, material engineering, biochemistry, etc., and unlike the conventionally known synthesis method, the present invention does not need protection and deprotection of protecting group, and thus it is expected that the present invention provides an effective synthetic method in synthesis and environmentally friendly aspects and ideal in an economic aspect.

While the invention has been shown and described with reference to certain exemplary embodiments thereof, it will be understood by those skilled in the related art that various changes in form and details may be made therein without departing from the scope of the invention as defined by the appended claims.

INDUSTRIAL AVAILABILITY

An imine having no substituent on a nitrogen according to the present invention can manufacture various binding products through a reaction with an external nucleophile, and the binding product produced by the method can be used as a useful compound in various fields such as pharmaceuticals, material engineering, biochemistry, etc. In addition, unlike the conventionally known synthesis method, the present invention does not need protection and deprotection of protecting group, and thus it is expected that the present invention provides an effective synthetic method in synthesis and environmentally friendly aspects and ideal in an economic aspect.

While the invention has been shown and described with reference to certain exemplary embodiments thereof, it will be understood by those skilled in the related art that various changes in form and details may be made therein without departing from the scope of the invention as defined by the appended claims.

What is claimed is:
1. A method of synthesizing an imine having no substituent on a nitrogen, comprising:
   adding a metal complex to an organic azide.
2. The method according to claim 1, wherein the metal complex is a ruthenium complex.
3. The method according to claim 2, wherein the ruthenium complex is a ruthenium complex of Formula 1 or Formula 2:

[Formula 1]

[Formula 2]

where $R_1$ and $R_2$ are each independently hydrogen, substituted or unsubstituted phenyl, or $C_1$~$C_5$ alkyl, and FG is amino, hydroxyl, amide, ester, or ether.
4. The method according to claim 1, wherein the synthesis is performed through irradiation of visible rays.
5. A method of manufacturing a binding product through addition of the imine manufactured in claim 1 with a nucleophile, wherein the addition is performed under neutral conditions without ammonia.
6. The method according to claim 5, wherein the binding product is an amine.
7. The method according to claim 5, wherein the nucleophile is selected from the group consisting of an organic metal compound, an organic carbon compound, and an organic heteroelement compound.

* * * * *